(12) United States Patent
Sugishita et al.

(10) Patent No.: US 7,125,565 B2
(45) Date of Patent: Oct. 24, 2006

(54) COMPOSITION IMPROVED IN THE SOLUBILITY OR ORAL ABSORBABILITY

(75) Inventors: Jun Sugishita, Sunto-gun (JP); Makoto Kigoshi, Sunto-gun (JP); Setsuko Yano, Sakai (JP); Hideki Morita, Chiyoda-ku (JP); Yasuki Kato, Sunto-gun (JP)

(73) Assignee: Kyowa Hakko Kogyo Co., Ltd., Tokyo ( * ) Notice: Subject to any disclaimer, the term of this patent is extended or adjusted under 35 U.S.C. 154(b) by 66 days.

(21) Appl. No.: 10/433,515

(22) PCT Filed: Nov. 30, 2001

(86) PCT No.: PCT/JP01/10488

§ 371 (c)(1),
(2), (4) Date: Nov. 24, 2003

(87) PCT Pub. No.: WO02/43704

PCT Pub. Date: Jun. 6, 2002

(65) Prior Publication Data

US 2004/0076675 A1    Apr. 22, 2004

(30) Foreign Application Priority Data

Dec. 1, 2000   (JP)  ............................. 2000-367040
Apr. 25, 2001  (JP)  ............................. 2001-127228

(51) Int. Cl.
*B01D 11/02* (2006.01)
(52) U.S. Cl. .................................... 424/489
(58) Field of Classification Search ............... 424/489
See application file for complete search history.

(56) References Cited

U.S. PATENT DOCUMENTS 4,794,111 A    12/1988  Posanski et al.

5,814,621 A    9/1998   Kanaya et al.

FOREIGN PATENT DOCUMENTS

| EP | 1 103 258 | 5/2001 |
| EP | 1 103 258 A1 * | 5/2001 |
| JP | 49-46585 | 5/1974 |
| JP | 56-110612 | 9/1981 |
| JP | 2000-86509 | 3/2000 |
| WO | WO 00/43408 | 7/2000 |

OTHER PUBLICATIONS

K Kakemi et al., "Mechanism of Drug Absorption from Micellar Solution", Chem. Pharm. Bull., 18(8)1563-1568(1970), pp. 1563-1569.

S. Solvang et al., "Effect of Tablet Processing and Formulation Factors on Dissolution Rate of the Active Ingredient in Human Gastric Juice", Journal of Pharmaceutical Sciences, vol. 59, No. 1, Jan. 1970, pp. 49-53.

J. Sxojtli, "Cyclodextrins in Drug Formulations: Part II", Pharmaceutical Technology, Aug. 1991, pp. 24f.

P. Finholt, "Influence of Formulation on Dissolution Rate", Dissolution Technology, The Industrial Pharmaceutical Technology Section of the Academy of Pharmaceutical Sciences.

* cited by examiner

*Primary Examiner*—Robert D. Harlan
(74) *Attorney, Agent, or Firm*—Eckert Seamans Cherin & Mellott, LLC

(57) ABSTRACT

An object of the present invention is to provide a composition improved in the solubility or oral absorbability.

The present invention provides a composition which comprises three components of a slightly water-soluble component, a surfactant and a hydrophilic polymer, and is obtainable by wet granulation in the presence of water.

32 Claims, 2 Drawing Sheets

COMPOSITION IMPROVED IN THE SOLUBILITY OR ORAL ABSORBABILITY

TECHNICAL FIELD

The present invention relates to a composition improved in the solubility or oral absorbability in a slightly water-soluble component.

BACKGROUND ART

In general, slightly water-soluble medicaments have poor oral absorbability because of their low solubility and low dissolution rate in the digestive tracts. Various methods have been investigated to improve the oral absorbability. Known examples of the methods include (a) a wet granulation method using a hydrophilic polymer, (b) a method in which the medicament is fined by grinding, (c) a method in which a solid dispersion is formed with a polymer material, (d) a method in which a soluble clathrate is formed together with cyclodextrins, (e) a method in which a surfactant is added, and the like.

The method (a) is known as a simple method in which the wettability to water of a medicament which is relatively water-insoluble can be improved to raise the dissolution rate thereof [*J. Pharm. Sci.*, 59, 49 (1970) etc.] However, the effect is so limitative that the oral absorbability of a medicament which is quite slightly water-soluble cannot be sufficiently improved.

The method (b) is known as a method for raising the dissolution rate of a slightly water-soluble medicament by increasing the surface area thereof [*Dissolution Technology*, the Industrial Pharmaceutical Technology Section of the Academy of Pharmaceutical Science, p. 108 (1974) etc.] However, the size to be fined by grinding is so limitative that there are some problems that particles are aggregated or hardly wettable and the like when the finely ground medicaments are dispersed in water. Although a combination of the method (a) and the method (b) is frequently used, this combination is still insufficient for improving the oral absorbability of a quite slightly water-soluble medicament.

When a solid dispersion is formed in the absence of water in accordance with the method (c) (Japanese Published Unexamined Patent Application No. 110612/81 etc.), the solubility of a slightly water-soluble medicament is transiently increased upon the dispersion of the solid dispersion in water. However, there is a problem that the medicament is crystallized after a definite period of time and thus the solubility thereof is decreased. In addition, it is known that the stability of a solid dispersion obtained by the method (c) is sometimes decreased when stored under highly humid conditions. Moreover, there is a further problem that an organic solvent such as a halogenated solvent which is problematic in safety is necessary in many cases in the step of preparing the solid dispersion of the medicament.

In the method (d), there are some medicaments which do not form a clathrate, because the formation of a clathrate depends on the structure of a medicament [*Pharmaceutical Technology*, 15, 24–38 (1991) etc.]

In the method (e), a large amount of a surfactant is necessary to improve the solubility of a quite slightly water-soluble medicament. However, since many surfactants are in the form of liquid or wax, they sometimes disturb the preparation of a solid product. Even if the solubility is improved, the oral absorbability is sometimes decreased by micellation due to a surfactant depending on the properties of the medicament [*Chemical & Pharmaceutical Bulletin*, 18(8), 1563 (1970) etc.]

As a method for improving the bioavailability of a steroid medicament which is less than 100 to 200 ng/ml, U.S. Pat. No. 4,684,636 discloses a method wherein beads made of a saccharide or the like are coated with an aqueous suspension containing the steroid medicament, a binder and an optional wetting agent and then are put into capsules. In this method, however, it is somewhat troublesome to produce the product and the effect is still insufficient because an area under curve (AUC) of the medicament concentration in plasma is not more than twice as large as that of a dry mixture of the medicament with an excipient free from a wetting agent.

Under these circumstances, the composition which is easily used and has high effects, in which a slightly water-soluble component has improved solubility or oral absorbability, has been required.

DISCLOSURE OF THE INVENTION

The present invention relates to the following (1) to (21).

(1) A composition which comprises three components of a slightly water-soluble component, a surfactant and a hydrophilic polymer, and is obtainable by wet granulation in the presence of water.

(2) The composition according to (1), wherein the slightly water-soluble component is a slightly water-soluble medicament.

(3) The composition according to (1), wherein the slightly water-soluble component is a slightly water-soluble food component.

(4) The composition according to any one of (1) to (3), which comprises an excipient.

(5) The composition according to any one of (1) to (4), wherein the surfactant is one or more surfactants selected from the group consisting of sodium lauryl sulfate, polysorbate 80, polysorbate 60, polyoxyethylene hydrogenated castor oil, polyoxyethylene polyoxypropylene glycol and sucrose fatty acid esters.

(6) The composition according to any one of (1) to (5), wherein the hydrophilic polymer is one or more hydrophilic polymers selected from the group consisting of hydroxypropyl cellulose, hydroxypropyl methyl cellulose, methyl cellulose, carboxymethyl cellulose, carboxymethyl ethyl cellulose, hydroxypropyl starch, hydroxyethyl cellulose, hydroxypropyl methyl cellulose acetate succinate, hydroxypropyl methyl cellulose phthalate, carboxyvinyl polymer, polyvinylpyrrolidone, polyvinyl alcohol, methacrylic acid copolymers, macrogol, starch, gelatin, dextrin, pullulan, agar and acacia.

(7) The composition according to any one of (1) to (5), wherein the hydrophilic polymer is one or more hydrophilic polymers selected from the group consisting of hydroxypropyl cellulose, hydroxypropyl methyl cellulose and polyvinylpyrrolidone.

(8) The composition according to any one of (4) to (7), wherein the excipient is one or more excipients selected from the group consisting of lactose, sucrose, starch, crystalline cellulose, D-mannitol, D-sorbitol, a starch derivative, a cellulose derivative, a carbonate, a phosphate and a sulfate.

(9) The composition according to any one of (4) to (7), wherein the excipient is one or more excipients selected from the group consisting of starch, crystalline cellulose and D-mannitol.

(10) The composition according to any one of (1) and (4) to (9), wherein the slightly water-soluble component is a steroid medicament.

(11) The composition according to any one of (1) and (4) to (9), wherein the slightly water-soluble component is a compound represented by formula (I) [hereinafter referred to as Compound (I)]:

wherein R represents $NR^1R^2$, in which $R^1$ and $R^2$ are the same or different and each represents hydrogen, substituted or unsubstituted alkyl, substituted or unsubstituted aryl or a substituted or unsubstituted aromatic heterocyclic group, or $R^1$ and $R^2$ form a substituted or unsubstituted heterocyclic group together with the adjacent nitrogen atom.

(12) The composition according to (11), wherein $R^1$ and $R^2$ are the same or different and each represents hydrogen or substituted or unsubstituted alkyl.

(13) The composition according to (11), wherein $R^1$ and $R^2$ are the same or different and each represents hydrogen or alkyl having 1 to 5 carbon atoms.

(14) The composition according to (11), wherein R is $NHCH_2CH_2CH_3$, $N(CH(CH_3)_2)_2$ or $NHC(CH_3)_3$.

(15) The composition according to any one of (1) to (4) and (8) to (14), wherein the surfactant is sodium lauryl sulfate, and the hydrophilic polymer is hydroxypropyl cellulose.

(16) The composition according to any one of (1) to (4) and (8) to (14), wherein the surfactant is sodium lauryl sulfate, and the hydrophilic polymer is hydroxypropyl methyl cellulose.

(17) The composition according to any one of (1) to (4) and (8) to (14), wherein the surfactant is sodium lauryl sulfate, and the hydrophilic polymer is polyvinylpyrrolidone.

(18) The composition according to any one of (1) to (17), wherein the wet granulation is carried out by a wet granulation method by stirring.

(19) The composition according to any one of (1) and (4) to (9), wherein the slightly water-soluble component is ubidecarenone or a fat-soluble vitamin.

(20) A method for improving the solubility of a slightly water-soluble component, which comprises subjecting the slightly water-soluble component to wet granulation together with a surfactant and a hydrophilic polymer in the presence of water.

(21) A method for improving the oral absorbability of a slightly water-soluble component, which comprises subjecting the slightly water-soluble component to wet granulation together with a surfactant and a hydrophilic polymer in the presence of water.

The composition of the present invention is not particularly limited, so long as it contains three components of a slightly water-soluble component, a surfactant and a hydrophilic polymer and is obtainable by wet granulation in the presence of water.

The slightly water-soluble component includes a slightly water-soluble medicament, a slightly water-soluble food component, and the like.

The slightly water-soluble medicament is not particularly limited, and includes any medicaments considered to be "slightly water-soluble" or "quite slightly soluble in water" according to The Pharmacopoeia of Japan. The slightly water-soluble medicament includes nifedipine, γ-oryzanol, indomethacin, rifampicillin, griseofulvin, mefenamic acid, corticosteroid, fenitoine, ubidecarenone (coenzyme $Q_{10}$), fat-soluble vitamins, steroid medicaments, nonsteroid medicaments, and the like.

The ubidecarenone in the present specification includes precursors, prodrugs and the like which can be converted into ubidecarenone in vivo.

The slightly water-soluble medicament is preferably a hydrophobic steroid medicament or a hydrophobic nonsteroid medicament.

The hydrophobic nonsteroid medicament includes xanthine medicaments, dibenzoxepine medicaments and the like, and is preferably Compound (II) which is a xanthine medicament:

wherein $R^3$ and $R^4$ are the same or different and each represents substituted or unsubstituted alkyl; and $R^5$ represents substituted or unsubstituted alkyl, substituted or unsubstituted cycloalkyl, substituted or unsubstituted bicycloalkyl, or substituted or unsubstituted tricycloalkyl, Compound (III) which is a dibenzoxepine medicament:

wherein $R^6$ and $R^7$ are the same or different and each represents substituted or unsubstituted alkyl; and $R^8$ represents halogen, or the like. Examples of Compound (II) include Compound (IIa) represented by the following formula (IIa):

Examples of Compound (III) include Compound (IIIa) represented by the following formula (IIIa):

(IIIa)

The hydrophobic nonsteroid medicament includes Compounds (I), and is preferably a compound which is Compound (I) wherein R represents NHCH$_2$CH$_2$CH$_3$, N(CH(CH$_3$)$_2$)$_2$ or NHC(CH$_3$)$_3$ [referred to as Compound (Ia), (Ib) or (Ic), respectively] or the like.

In the definition of each group in Compounds (I) to (III), the alkyl includes linear or branched alkyl having, for example, 1 to 15 carbon atoms, such as methyl, ethyl, propyl, isopropyl, butyl, isobutyl, tert-butyl, pentyl, hexyl, heptyl, octyl, nonyl, decyl, undecyl, dodecyl, tridecyl, tetradecyl and pentadecyl.

The aryl includes aryl having, for example, 6 to 14 carbon atoms, such as phenyl, naphthyl and anthryl.

The aromatic heterocyclic group includes a 3- to 8-membered monocyclic aromatic heterocyclic group containing at least one atom selected from a nitrogen atom, an oxygen atom and a sulfur atom, a fused bicyclic or tricyclic aromatic heterocyclic group in which 3- to 8-membered rings are fused, containing at least one atom selected from a nitrogen atom, an oxygen atom and a sulfur atom, and the like. Examples include furyl, thienyl, pyrrolyl, imidazolyl, pyrazolyl, triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl, furazanyl, pyridyl, pyrimidinyl, pyrazinyl, pyridazinyl, quinolyl, quinoxalinyl, isoquinolyl, quinazolinyl, phthalazinyl, purinyl, indolyl, indazolyl, benzimidazolyl, isoindolyl, 2-pyridonyl, 4-pyridonyl, uracilyl, benzofuryl, benzothienyl and the like.

The heterocyclic group formed together with the adjacent nitrogen atom includes a 5- or 6-membered monocyclic heterocyclic group containing at least one nitrogen atom (the monocyclic heterocyclic group may contain other nitrogen atom(s), oxygen atom(s) or sulfur atom(s)), a fused bicyclic or tricyclic heterocyclic group in which 3- to 8-membered rings are fused together, containing at least one nitrogen atom (the fused heterocyclic group may contain other nitrogen atom(s), oxygen atom(s) or sulfur atom(s)), and the like. Examples include pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, pyrrolyl, imidazolyl, pyrazolyl and the like.

The cycloalkyl includes cycloalkyl having, for example, 3 to 9 carbon atoms such as cyclopropyl, cyclobutyl, cyclopentyl, cyclohexyl, cycloheptyl, cyclooctyl and cyclononyl.

The bicycloalkyl includes bicycloalkyl having, for example, 7 to 12 carbon atoms such as bicyclo[2.2.1]heptyl, bicyclo[2.2.2]octyl and bicyclo[3.3.1]nonyl.

The tricycloalkyl includes tricycloalkyl having, for example, 9 or 10 carbon atoms such as adamantyl and n-adamantyl.

The halogen includes a fluorine atom, a chlorine atom, a bromine atom and an iodine atom.

The substituents in the substituted alkyl, the substituted cycloalkyl, the substituted bicycloalkyl and the substituted tricycloalkyl are the same or different and, for example, 1 to 3 substituents such as hydroxy or halogen. The substituents in the substituted aryl, the substituted aromatic heterocyclic group and the substituted heterocyclic group formed together with the adjacent nitrogen atom are the same or different and, for example, 1 to 3 substituents such as alkyl, hydroxy or halogen. In the above definitions, the alkyl and the halogen have the same meanings as defined above, respectively.

The slightly water-soluble medicament can be used either as a free form (i.e., a form in which a salt is not formed) or as a pharmaceutically acceptable salt. As for the pharmaceutically acceptable salt, examples include pharmaceutically acceptable acid addition salts, metal salts, ammonium salts, organic amine addition salts, amino acid addition salts and the like. The acid addition salts include inorganic acid salts such as hydrochlorides, hydrobromides, sulfates, phosphates and nitrates; and organic acid salts such as acetates, fumarates, maleates, tartrates, citrates, lactates, oxalates, methanesulfonates, benzenesulfonates and p-toluenesulfonates. The metal salts include alkali metal salts such as lithium salts, sodium salts and potassium salts; alkaline earth metal salts such as magnesium salts and calcium salts; aluminum salts; zinc salts; and the like. The ammonium salts include salts of ammonium, tetramethylammonium and the like. The organic amine addition salts include addition salts of morpholine, piperidine or the like. The amino acid addition salts include addition salts of glycine, phenylalanine, aspartic acid, glutamic acid, lysine or the like.

The slightly water-soluble food component includes ubidecarenone, fat-soluble vitamins and the like.

The fat-soluble vitamins include vitamin A, vitamin D, vitamin E, vitamin F, vitamin K, vitamin U and the like, and a preferable fat-soluble vitamin is vitamin K. Further, "fat-soluble vitamins" in the present specification also include precursors, prodrugs and the like of vitamin A, vitamin D, vitamin E, vitamin F, vitamin K, vitamin U and the like which can be converted into these vitamins in vivo.

The slightly water-soluble food component can be used either as a free form (i.e., a form in which a salt is not formed) or as a salt. The salt of the slightly water-soluble food component includes salts exemplified as the above pharmaceutically acceptable salts of the slightly water-soluble medicament.

The surfactant is not particularly limited, so long as it can be orally administered. Examples include sodium lauryl sulfate, polysorbate 80, polysorbate 60, polysorbate 40, polysorbate 20, poloxyl 10 oleyl ether, poloxyl 20 cetostearyl ether, poloxyl 20 cetyl ether, polyoxyethylene hydrogenated castor oil, poloxyl 40 stearate, poloxyl 50 stearate, polyoxyethylene polyoxypropylene glycol, sucrose fatty acid esters and the like, which may be used in combination of two or more thereof. Preferable examples include sodium lauryl sulfate, polysorbate 80, polysorbate 60, polyoxyethylene hydrogeneated castor oil, polyoxyethylene polyoxypropylene glycol, sucrose fatty acid esters and the like (two or more surfactants selected from sodium lauryl sulfate, polysorbate 80, polysorbate 60, polyoxyethylene hydrogenated castor oil, polyoxyethylene polyoxypropylene glycol and sucrose fatty acid esters may be used in combination).

More preferable examples include sodium lauryl sulfate, polysorbate 80, sucrose fatty acid esters and the like (two or more surfactants selected from sodium lauryl sulfate, polysorbate 80 and sucrose fatty acid esters may be used in combination).

The hydrophilic polymer is not particularly limited, so long as it is soluble in water or swellable in water and can be used as a binder. Non-limited examples include hydroxypropyl cellulose, hydroxypropyl methyl cellulose, methyl cellulose, carboxymethyl cellulose, carboxymethyl ethyl cellulose, hydroxypropyl starch, hydroxyethyl cellulose, hydroxypropyl methyl cellulose acetate succinate, hydroxypropyl methyl cellulose phthalate, carboxyvinyl polymer, polyvinylpyrrolidone, polyvinyl alcohol, methacrylic acid copolymers, macrogol, starch, gelatin, dextrin, pullulan, agar, acacia and the like, which may be used in combination of two or more thereof. Preferable examples include hydroxypropyl cellulose, hydroxypropyl methyl cellulose, polyvinylpyrrolidone and the like (two or more hydrophilic polymers selected from hydroxypropyl cellulose, hydroxypropyl methyl cellulose and polyvinylpyrrolidone may be used in combination).

The content of the slightly water-soluble component in the composition of the present invention is not particularly limited, and is preferably 0.0001 to 0.5 g, more preferably 0.01 to 0.3 g, per gram of the composition.

The weight ratio of the slightly water-soluble component to the surfactant and hydrophilic polymer is not particularly limited, and the ratio of slightly water-soluble component:surfactant:hydrophilic polymer is preferably 1:0.1 to 50:0.01 to 20, more preferably 1:0.5 to 20:0.1 to 10.

The slightly water-soluble component, surfactant and hydrophilic polymer to be used in the present invention may be obtained as commercially available products or produced by known methods. Particularly, Compounds (I), (II) and (III), including novel compounds, can be produced, respectively by the methods described in WO 00/43408, Japanese Published Unexamined Patent Application No. 173889/91, Japanese Published Unexamined Patent Application No. 132477/93 and the like or by modified methods thereof. The desired compound in the production process can be isolated and purified according to the conventional purification method used in the field of synthetic organic chemistry such as filtration, extraction, washing, drying, concentration, recrystallization or various chromatographies. In the production of a salt of Compound (I), (II) or (III), when Compound (I), (II) or (III) is obtained in the form of a salt, it may be purified as such, and when Compound (I), (II) or (III) is in the form of a free salt, it may be dissolved or suspended in an appropriate solvent and then an acid or base is added thereto to form a salt.

The wet granulation in the present invention represents production of granulated powder having an almost uniform shape and size from a wet powdery or block material, preferably production of granulated powder having an almost uniform shape and size from a wet powdery material. The addition of the hydrophilic polymer during the wet granulation may be carried out by a method in which the hydrophilic polymer is added in a solid state or a method in which the hydrophilic polymer is dissolved in an aqueous solvent and then added as a solution.

The aqueous solvent used in the wet granulation in the present invention includes water and a water/organic solvent mixture. Examples include water, water/ethanol, water/isopropyl alcohol, water/acetone and the like, and water is preferred. The weight of the aqueous solvent used in the wet granulation in the present invention is not particularly limited, and it is preferable to use the slightly water-soluble component and the aqueous solvent at a weight ratio of 1:0.01 to 0.5, the weight ratio having more preferably 1:0.05 to 0.2. As an apparatus used for the granulation procedure in the present invention, any granulation apparatuses usually used, such as a stirring type, a flow type, a roll-flow type or an extrusion type, can be used without limitation. A mortar or the like may also be used.

The composition of the present invention may contain an excipient. For example, an excipient may be added during the granulation procedure as described above.

The excipient is not particularly limited, and includes lactose, sucrose, starch, crystalline cellulose, D-mannitol, D-sorbitol, starch derivatives (corn starch etc.), cellulose derivatives, carbonates, phosphates, sulfates and the like, which may be used alone or in combination of two or more thereof. Preferable examples include D-mannitol, lactose, D-mannitol/starch, lactose/starch, D-mannitol/crystalline cellulose, lactose/crystalline cellulose, D-mannitol/starch/crystalline cellulose, lactose/starch/crystalline cellulose and the like. More preferable examples include starch, crystalline cellulose, D-mannitol and the like (two or more excipients selected from starch, crystalline cellulose and D-mannitol may be used in combination). D-Manntiol/starch is still more preferable.

In the present invention, the excipient can be used in an amount of 0- to 1000-folds by weight as much as the slightly water-soluble component (Use of 0-fold by weight of the excipient as much as the slightly water-soluble component means that no excipient is used).

In addition, the composition of the present invention may contain a disintegrator, a lubricant or the like, if necessary. The disintegrator includes crospovidone, croscarmellose sodium, sodium carboxymethyl starch, low substituted hydroxypropyl cellulose and the like, although it is not limited thereto. The lubricant includes magnesium stearate, calcium stearate, talc, glyceryl monostearate, light anhydrous silicic acid and the like.

Furthermore, the composition of the present invention may contain a coloring agent, a flavor or the like, if necessary. The coloring agent includes titanium oxide, talc, ferric oxide, yellow ferric oxide, black iron oxide, copper chlorophyll, copper chlorophylline sodium, carbon black, carbon for medical use, various edible colorants, glycyrrhiza extract, green tea powder, riboflavin, riboflavin butyrate, riboflavin sodium phosphate, octyldodecyl myristate and the like. The flavor includes fennel powder, fennel oil, ethyl vanillin, orange extract, orange oil, orange essence, capsicum flavor, glycyrrhiza extract, cinnamon bark powder, cinnamon oil, cherry flavor, clove oil, turpentine oil, bitter orange peel powder, peppermint oil, vanilla flavor, vanillin, bitter essence, bergamot flavor, menthol, eucalyptus oil, borneol, rosin and the like.

The composition of the present invention can be formulated into granules or fine granules. Also, it can be encapsulated to give capsules or tableted to give tablets.

BRIEF DESCRIPTION OF THE DRAWINGS

Symbols used in FIGS. 1 and 2 are described below.

-○-: Changes in the concentration of Compound (Ia) in plasma when the composition of Example 11 was orally administered.

-□-: Changes in the concentration of Compound (Ia) in plasma when the composition of Comparative Example 4 was orally administered.

-Δ-: Changes in the concentration of Compound (Ia) in plasma when the composition of Comparative Example 5 was orally administered.

- -: Changes in the concentration of Compound (Ib) in plasma when the composition of Example 28 was orally administered.

--○--: Changes in the concentration of Compound (Ib) in plasma when the composition of Example 29 was orally administered.

-▲-: Changes in the concentration of Compound (Ib) in plasma when the composition of Example 30 was orally administered.

--□--: Changes in the concentration of Compound (Ib) in plasma when the composition of Example 31 was orally administered.

-■-: Changes in the concentration of Compound (Ib) in plasma when the injection of Comparative Example 11 was intravenously administered.

BEST MODE FOR CARRYING OUT THE INVENTION

The present invention is described below in detail based on Examples. However, the present invention is not limited thereto.

EXAMPLE 1

In a mortar, 0.05 g of Compound (Ia), 0.1 g of sodium lauryl sulfate, 0.6 g of D-mannitol, 0.25 g of corn starch and 0.02 g of hydroxypropyl cellulose (HPC-SSL) were granulated by kneading with a pestle while water was dropped thereto. After drying at 60° C. for 30 minutes, the granulated powder was sifted out with a sieve of 420 μm mesh to give a powdery solid composition.

EXAMPLE 2

In a mortar, 0.1 g of Compound (Ia), 0.2 g of sodium lauryl sulfate, 1.16 g of D-mannitol, 0.5 g of corn starch and 0.04 g of hydroxypropylmethyl cellulose were granulated by kneading with a pestle while water was dropped thereto. After drying at 60° C. for 1 hour, the granulated powder was sifted out with a sieve of 500 μm mesh to give a powdery solid composition.

EXAMPLE 3

In a mortar, 0.1 g of Compound (Ia), 0.2 g of sodium lauryl sulfate, 1.16 g of D-mannitol, 0.5 g of corn starch and 0.04 g of polyvinylpyrrolidone were granulated by kneading with a pestle while water was dropped thereto. After drying at 60° C. for 1 hour, the granulated powder was sifted out with a sieve of 500 μm mesh to give a powdery solid composition.

EXAMPLE 4

In a high-shear mixer type tablet mill, 0.5 g of Compound (Ia), 1.0 g of sodium lauryl sulfate, 5.8 g of D-mannitol, 2.5 g of corn starch and 0.2 g of hydroxyproypl cellulose (HPC-SSL) were fed and granulated for about 5 minutes while water was dropped thereto. After drying at 60° C. for 1 hour, the granulated powder was sifted out with a sieve of 500 μm mesh to give a granular solid composition.

EXAMPLE 5

In a high-shear mixer type tablet mill, 0.5 g of Compound (Ia), 1.0 g of sodium lauryl sulfate, 5.8 g of D-mannitol and 2.5 g of corn starch were fed and granulated for about 5 minutes while 1.2 g of an aqueous solution of 16.7% by weight hydroxypropyl cellulose (HPC-SSL) and a small amount of water were dropped thereto. After drying at 60° C. for 1 hour, the granulated powder was sifted out with a sieve of 500 μm mesh to give a granular solid composition.

EXAMPLE 6

A tablet was obtained by mixing 0.2 g of the solid composition obtained in Example 4 with 0.01 g of crospovidone and compressing them in an oil hydraulic press under 3 MPa pressure.

EXAMPLE 7

In a high-shear mixer type tablet mill, 0.5 g of Compound (Ia), 0.5 g of sodium lauryl sulfate, 6.3 g of D-mannitol, 2.5 g of corn starch and 0.2 g of hydroxyproypl cellulose (HPC-SSL) were fed and granulated for about 5 minutes while water was dropped thereto. After drying at 60° C. for 1 hour, the granulated powder was sifted out with a sieve of 500 μm mesh to give a granular solid composition (In the composition of Example 7, the added amount of sodium lauryl sulfate is a half of that of the sodium lauryl sulfate in the composition of Example 4).

EXAMPLE 8

In a high-shear mixer type tablet mill, 0.5 g of Compound (Ia), 1.0 g of sodium lauryl sulfate, 5.7 g of D-mannitol, 2.5 g of corn starch and 0.3 g of hydroxyproypl cellulose (HPC-SSL) were fed and granulated for about 5 minutes while water was dropped thereto. After drying at 60° C. for 1 hour, the granulated powder was sifted out with a sieve of 500 μm mesh to give a granular solid composition (In the composition of Example 8, the added amount of hydroxyproypl cellulose (HPC-SSL) is 1.5-folds higher than that of the hydroxyproypl cellulose (HPC-SSL) in the composition of Example 4).

EXAMPLE 9

In a high-shear mixer type tablet mill, 0.5 g of Compound (Ia), 1.0 g of sodium lauryl sulfate, 5.9 g of D-mannitol, 2.5 g of corn starch and 0.1 g of hydroxyproypl cellulose (HPC-SSL) were fed and granulated for about 5 minutes while water was dropped thereto. After drying at 60° C. for 1 hour, the granulated powder was sifted out with a sieve of 500 μm mesh to give a granular solid composition (In the composition of Example 9, the added amount of hydroxyproypl cellulose (HPC-SSL) is a half of that of the hydroxyproypl cellulose (HPC-SSL) in the composition of Example 4).

EXAMPLE 10

In a high-shear mixer type tablet mill, 0.5 g of Compound (Ia), 1.0 g of sodium lauryl sulfate, 5.8 g of D-mannitol, 2.5 g of corn starch and 0.2 g of hydroxyproypl cellulose (HPC-SSL) were fed and granulated for about 15 minutes while water was dropped thereto. After drying at 60° C. for 1 hour, the granulated powder was sifted out with a sieve of 500 μm mesh to give a granular solid composition (The granulation time in Example 10 is different from that in Example 4).

EXAMPLE 11

A capsule preparation was obtained by filing 0.2 g of the solid composition obtained in Example 4 (corresponding to 0.01 g of Compound (Ia)) in a gelatin capsule (manufactured by Shionogi Qualicaps).

EXAMPLE 12

A powdery solid composition was obtained by carrying out wet granulation, drying and sieving in the same manner as in Example 1 by using Compound (Ib) instead of Compound (Ia).

EXAMPLE 13

A powdery solid composition was obtained by carrying out wet granulation, drying and sieving in the same manner as in Example 1 by using Compound (Ic) instead of Compound (Ia).

EXAMPLE 14

In a mortar, 0.6 g of Compound (IIa), 1.2 g of sodium lauryl sulfate and 0.24 g of hydroxypropyl cellulose (HPC-SSL) were granulated by kneading with a pestle while water was dropped thereto. After drying at 60° C. for 60 minutes, a powdery solid composition was obtained.

EXAMPLE 15

In a mortar, 0.6 g of Compound (IIIa), 1.2 g of sodium lauryl sulfate and 0.24 g of hydroxypropyl cellulose (HPC-SSL) were granulated by kneading with a pestle while water was dropped thereto. After drying at 60° C. for 60 minutes, a powdery solid composition was obtained.

EXAMPLE 16

In a mortar, 0.1 g of ubidecarenone, 0.2 g of sodium lauryl sulfate, 1.66 g of D-mannitol and 0.04 g of hydroxyproypl cellulose (HPC-SSL) were granulated by kneading with a pestle for about 2 minutes while water was dropped thereto. After drying at 40° C. for 1 hour, the granulated powder was sifted out with a sieve of 500 μm mesh to give a powdery solid composition.

EXAMPLE 17

In a mortar, 0.1 g of ubidecarenone, 0.2 g of sodium lauryl sulfate, 1.66 g of D-mannitol and 0.04 g of hydroxyproypl cellulose (HPC-SSL) were granulated by kneading with a pestle for about 10 minutes while water was dropped thereto. After drying at 40° C. for 1 hour, the granulated powder was sifted out with a sieve of 500 μm mesh to give a powdery solid composition.

EXAMPLE 18

In a mortar, 1.2 g of ubidecarenone was mixed with 1.8 g of sodium lauryl sulfate for 3 minutes, and 2.5 g of the mixture, 7.2 g of D-mannitol and 0.3 g of hydroxyproypl cellulose (HPC-SSL) were fed in a high-shear mixer type tablet mill and granulated for about 25 minutes while water was dropped thereto. After drying at 40° C. for 2 hours, the granulated powder was sifted out with a sieve of 500 μm mesh to give a granular solid composition.

EXAMPLE 19

In a high-shear mixer type tablet mill, 0.5 g of Compound (Ib) having an average particle diameter size of 3 μm, 1.0 g of sodium lauryl sulfate, 5.8 g of D-mannitol, 2.5 g of corn starch and 0.2 g of hydroxyproypl cellulose (HPC-SSL) were fed and granulated for about 4 minutes while water was dropped thereto. After drying at 60° C. for 2 hours, the granulated powder was sifted out with a sieve of 500 μm mesh to give a granular solid composition.

EXAMPLE 20

In a high-shear mixer type tablet mill, 0.5 g of Compound (Ib) having an average particle diameter size of 29 μm, 1.0 g of sodium lauryl sulfate, 5.8 g of D-mannitol, 2.5 g of corn starch and 0.2 g of hydroxyproypl cellulose (HPC-SSL) were fed and granulated for about 4 minutes while water was dropped thereto. After drying at 60° C. for 2 hours, the granulated powder was sifted out with a sieve of 500 μm mesh to give a granular solid composition.

EXAMPLE 21

In a high-shear mixer type tablet mill, 0.5 g of Compound (Ib) having an average particle diameter size of 29 μm, 1.0 g of sodium lauryl sulfate and 0.2 g of hydroxyproypl cellulose (HPC-SSL) were fed and granulated for about 5 minutes while water was dropped thereto. Further, 5.8 g of D-mannitol and 2.5 g of corn starch was added thereto and the mixture was granulated for about 30 minutes while water was dropped thereto. After drying at 60° C. for 2 hours, the granulated powder was sifted out with a sieve of 500 μm mesh to give a granular solid composition.

EXAMPLE 22

Using a jet mill, 1.0 g of Compound (Ib) having an average particle diameter size of 94 μm and 2.0 g of sodium lauryl sulfate were ground to give a ground product. In a high-shear mixer type tablet mill, 1.5 g of the ground product, 5.8 g of D-mannitol, 2.5 g of corn starch and 0.2 g of hydroxyproypl cellulose (HPC-SSL) were fed and granulated for about 4 minutes while water was dropped thereto. After drying at 60° C. for 2 hours, the granulated powder was sifted out with a sieve of 500 μm mesh to give a granular solid composition.

EXAMPLE 23

In a high-shear mixer type tablet mill, 0.5 g of Compound (Ib) having an average particle diameter size of 5 μm, 1.0 g of sodium lauryl sulfate, 5.8 g of D-mannitol, 2.5 g of corn starch and 0.2 g of hydroxyproypl cellulose (HPC-SSL) were fed and granulated for about 4 minutes while water was dropped thereto. After drying at 60° C. for 2 hours, the granulated powder was sifted out with a sieve of 500 µm mesh to give a granular solid composition.

EXAMPLE 24

In a high-shear mixer type tablet mill, 0.5 g of Compound (Ib) having an average particle diameter size of 5 µm, 1.0 g of jet-ground sodium lauryl sulfate, 5.8 g of D-mannitol, 2.5 g of corn starch and 0.2 g of hydroxyproypl cellulose (HPC-SSL) were fed and granulated for about 7 minutes while water was dropped thereto. After drying at 60° C. for 2 hours, the granulated powder was sifted out with a sieve of 500 µm mesh to give a granular solid composition.

EXAMPLE 25

In a high-shear mixer type tablet mill, 0.5 g of Compound (Ib) having an average particle diameter size of 5 µm, 1.0 g of sodium lauryl sulfate, 8.3 g of D-mannitol and 0.2 g of hydroxyproypl cellulose (HPC-SSL) were fed and granulated for about 3 minutes while water was dropped thereto. After drying at 60° C. for 2 hours, the granulated powder was sifted out with a sieve of 500 µm mesh to give a granular solid composition.

EXAMPLE 26

In a high-shear mixer type tablet mill, 0.5 g of Compound (Ib) having an average particle diameter size of 5 µm, 1.0 g of sodium lauryl sulfate, 5.8 g of D-mannitol, 2.5 g of corn starch and 0.2 g of hydroxyproypl cellulose (HPC-SSL) were fed and granulated for about 4 minutes while water was dropped thereto. After drying at 60° C. for 2 hours, the granulated powder was sifted out with a sieve of 500 µm mesh to give a granular solid composition.

EXAMPLE 27

In a vinyl bag, 0.5 g of Compound (Ib) having an average particle diameter size of 5 µm, 1.0 g of sodium lauryl sulfate and 0.2 g of hydroxyproypl cellulose (HPC-SSL) were mixed together for 1 minute. Separately, in a vinyl bag, 5.8 g of D-mannitol and 2.5 g of corn starch were mixed together for 1 minute. Both of the mixtures were fed in a high-shear mixer type tablet mill and granulated for about 4 minutes while water was dropped thereto. After drying at 60° C. for 2 hours, the granulated powder was sifted out with a sieve of 500 µm mesh to give a granular solid composition.

EXAMPLE 28

A capsule preparation was obtained by filling 0.2 g of the solid composition obtained in Example 19 (corresponding to 0.01 g of Compound (Ib)) in a gelatin capsule (manufactured by Shionogi Qualicaps).

EXAMPLE 29

A capsule preparation was obtained by filling 0.2 g of the solid composition obtained in Example 20 (corresponding to 0.01 g of Compound (Ib)) in a gelatin capsule (manufactured by Shionogi Qualicaps).

EXAMPLE 30

A capsule preparation was obtained by filing 0.2 g of the solid composition obtained in Example 21 (corresponding to 0.01 g of Compound (Ib)) in a gelatin capsule (manufactured by Shionogi Qualicaps).

EXAMPLE 31

A capsule preparation was obtained by filling 0.2 g of the solid composition obtained in Example 22 (corresponding to 0.01 g of Compound (Ib)) in a gelatin capsule (manufactured by Shionogi Qualicaps).

COMPARATIVE EXAMPLE 1

In a mortar, 0.05 g of Compound (Ia), 0.1 g of sodium lauryl sulfate, 0.6 g of D-mannitol, 0.25 g of corn starch and 0.02 g of hydroxypropyl cellulose (HPC-SSL) were mixed with a pestle to give a powdery solid composition (As the difference, wet granulation is carried out in Example 1, whereas wet granulation is not carried out in Comparative Example 1).

COMPARATIVE EXAMPLE 2

In a mortar, 0.05 g of Compound (Ia), 0.1 g of sodium lauryl sulfate, 0.6 g of D-mannitol and 0.25 g of corn starch were granulated by kneading with a pestle while water was dropped thereto. After drying at 60° C. for 30 minutes, the granulated powder was sifted out with a sieve of 420 µm mesh to give a powdery solid composition (As the difference, the solid composition of Example 1 contains a hydrophilic polymer, whereas the solid composition of Comparative Example 2 contains no hydrophilic polymer).

COMPARATIVE EXAMPLE 3

In a mortar, 0.05 g of Compound (Ia), 0.6 g of D-mannitol, 0.25 g of corn starch and 0.02 g of hydroxypropyl cellulose (HPC-SSL) were granulated by kneading with a pestle while water was dropped thereto. After drying at 60° C. for 30 minutes, the granulated powder was sifted out with a sieve of 420 µm mesh to give a powdery solid composition (As the difference, the solid composition of Example 1 contains a surfactant, whereas the solid composition of Comparative Example 3 contains no surfactant).

COMPARATIVE EXAMPLE 4

In a mortar, 0.1 g of Compound (Ia) and 0.9 g of D-mannitol were mixed in a mortar. Then 0.1 g of this mixture (corresponding to 0.01 g of Compound (Ia)) was filled in a gelatin capsule (manufactured by Shionogi Qualicaps) to give a capsule preparation.

COMPARATIVE EXAMPLE 5

In a mortar, 0.1 g of Compound (Ia), 0.2 g of sodium lauryl sulfate and 0.9 g of D-mannitol were mixed. A capsule preparation was obtained by filling 0.12 g of the mixture (corresponding to 0.01 g of Compound (Ia)) in a gelatin capsule (manufactured by Shionogi Qualicaps).

COMPARATIVE EXAMPLE 6

A powdery solid composition was obtained by mixing the same components in a mortar at the same ratio as in Example 12.

COMPARATIVE EXAMPLE 7

A powdery solid composition was obtained by mixing the same components in a mortar at the same ratio as in Example 13.

COMPARATIVE EXAMPLE 8

In a mortar, 0.6 g of Compound (IIa), 1.2 g of sodium lauryl sulfate and 0.24 g of hydroxypropyl cellulose (HPC-SSL) were mixed to give a powdery solid composition.

COMPARATIVE EXAMPLE 9

In a mortar, 0.6 g of Compound (IIIa), 1.2 g of sodium lauryl sulfate and 0.24 g of hydroxypropyl cellulose (HPC-SSL) were mixed to give a powdery solid composition.

COMPARATIVE EXAMPLE 10

In a mortar, 0.15 g of ubidecarenone, 0.3 g of sodium lauryl sulfate, 2.49 g of D-mannitol and 0.06 g of hydroxypropyl cellulose (HPC-SSL) were mixed with a pestle to give a powdery solid composition.

COMPARATIVE EXAMPLE 11

In 30 ml of special grade ethanol, 0.03 g of Compound (Ib) was dissolved, and then 0.9 ml of polysorbate 80 was added thereto and dissolved therein. After removing the ethanol by stirring under a nitrogen gas stream, 30 ml of physiological saline (manufactured by Otsuka Pharmaceutical) was added to the residue to give an injection containing 1 mg/ml of Compound (Ib).

TEST EXAMPLE 1

An amount corresponding to 10 mg of Compound (Ia) of each of the solid compositions obtained in Examples 1 to 10 and Comparative Examples 1 to 3 was poured into 20 ml of water at 37° C. Under paddle-stirring at 50 rpm, the solution was sampled at 0.5 ml with the lapse of time and filtered through a filter of 0.2 μm mesh. Then, the solubility of Compound (Ia) was measured by high-performance liquid chromatography.

Table 1 shows changes in the solubility of Compound (Ia) with the lapse of time.

TABLE 1

Changes in solubility of Compound (Ia)
Dissolution test in 20 ml of water at 37° C.

| | Solubility (μg/ml) | | | |
|---|---|---|---|---|
| | 5 min | 15 min | 30 min | 60 min |
| Example 1 | 35.64 | 35.44 | 35.36 | 38.98 |
| Example 2 | 18.61 | 18.10 | 18.83 | 18.09 |
| Example 3 | 26.18 | 24.65 | 23.98 | 23.92 |
| Comparative Example 1 | 4.26 | 3.78 | 3.88 | 4.06 |
| Comparative Example 2 | 2.09 | 3.28 | 2.94 | 2.21 |
| Comparative Example 3 | 1.86 | 1.91 | 0.50 | 0.16 |

TABLE 1-continued

Changes in solubility of Compound (Ia)
Dissolution test in 20 ml of water at 37° C.

| | Solubility (μg/ml) | | | |
|---|---|---|---|---|
| | 5 min | 15 min | 30 min | 60 min |
| Example 4 | 29.02 | 27.77 | 26.98 | 29.20 |
| Example 5 | 26.61 | 28.38 | 30.26 | 32.26 |
| Example 6 | 11.54 | 23.13 | 23.96 | 23.70 |
| Example 7 | 28.60 | 28.49 | 25.58 | 25.90 |
| Example 8 | 15.14 | 14.26 | 14.86 | 14.00 |
| Example 9 | 23.11 | 22.67 | 22.83 | 22.71 |
| Example 10 | 117.14 | 118.06 | 116.09 | — |

As is apparent from Table 1, the solid compositions obtained in Examples 1 to 10 showed higher solubility and solubility than the solid compositions obtained in Comparative Examples 1 to 3, and kept the high solubility even after 1 hour passed.

In the solid compositions of Examples 2 and 3 in which different hydrophilic polymers were used, the high solubility was kept.

TEST EXAMPLE 2

Solubility of the capsule preparations obtained in Example 11 and Comparative Examples 4 and 5 were tested in the same manner as in Test Example 1. Table 2 shows changes in solubility of Compound (Ia) with the lapse of time.

TABLE 2

Changes in solubility of compound (Ia)
Dissolution test in 20 ml of water at 37° C.

| | Solubility (μg/ml) | | | |
|---|---|---|---|---|
| | 5 min | 15 min | 30 min | 60 min |
| Example 11 | 17.12 | 22.42 | 25.07 | 25.23 |
| Comparative Example 4 | 0.11 | 0.32 | 0.19 | 0.10 |
| Comparative Example 5 | 1.10 | 2.12 | 1.60 | 0.90 |

TEST EXAMPLE 3

Figure 1:
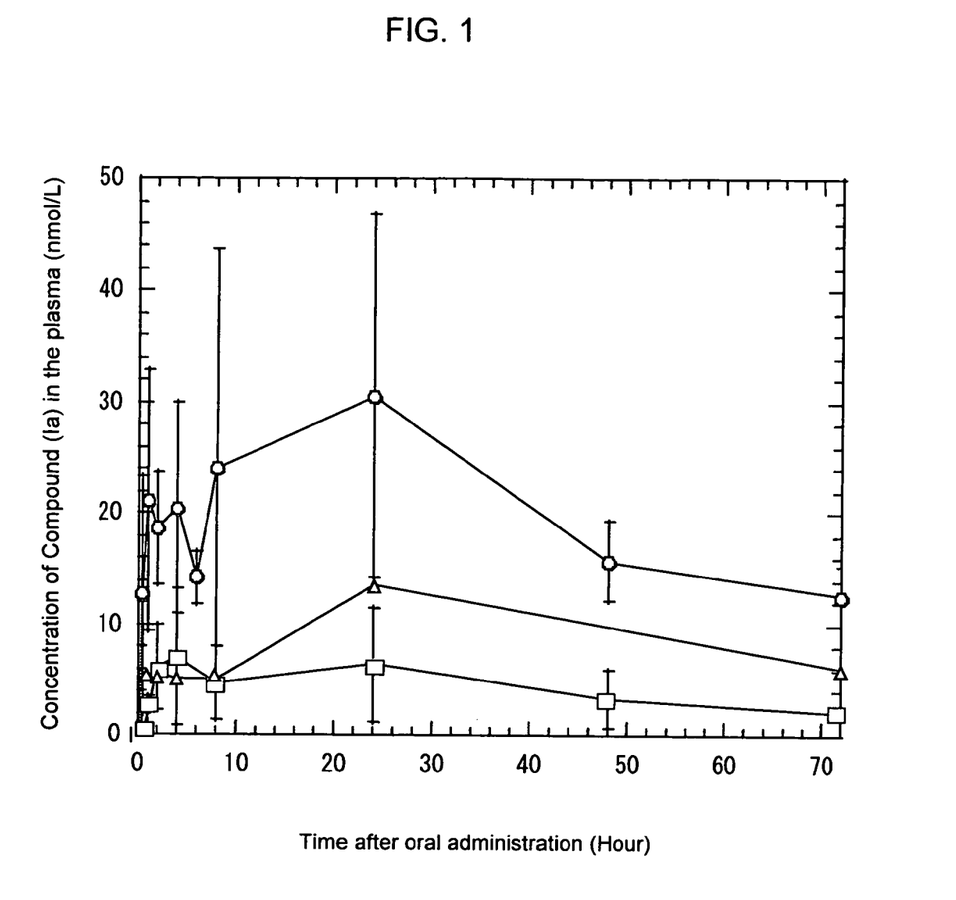
FIG. 1 shows changes in the concentration of Compound (Ia) in the plasma when a solid composition containing 0.01 g of Compound (Ia) was administered to a beagle.

Oral absorbability (dog) of the capsule preparations obtained in Example 11 and Comparative Examples 4 and 5 was evaluated. One capsule of each preparations was orally administered to a beagle and the blood of the animal was collected at definite intervals. Next, the concentration of Compound (Ia) in the plasma was measured by a high-performance liquid chromatography and the pharmacodynamic parameter was calculated. Regarding the capsules of Example 11 and Comparative Example 4, the mean and standard deviation of 3 cases were calculated, while concerning the capsule preparation of Comparative Example 5, the mean and standard deviation of 2 cases were calculated. FIG. 1 shows changes in the concentration in plasma and Table 3 shows pharmacodynamic parameters. In Table 3, Tmax, Cmax and $AUC_{0-\infty}$ represent the time necessary for reaching the maximum concentration in blood (the time necessary for reaching the peak of the curve of concentration in blood), the maximum concentration in blood (the concentration at the peak of the curve of concentration in blood), and the area under the curve of concentration in blood from the initiation of the administration to the disappearance of the medicament (the area under curve).

TABLE 3

| | Pharmacodynamic parameter | | |
|---|---|---|---|
| | Tmax (h) | Cmax (nmol/l) | $AUC_{0-\infty}$ (nmol · h/l) |
| Example 11 | 11.0 ± 11.8 | 42.4 ± 9.1 | 2865.7 ± 805.8 |
| Comparative Example 4 | 10.0 ± 12.1 | 7.5 ± 5.8 | 417.8 ± 310.1 |
| Comparative Example 5 | 13.0 | 14.3 | 1078.0 |

As is apparent from Tables 2 and 3 and FIG. 1, the capsule preparation of Example 11 prepared by encapsulating the composition of the present invention showed higher solubility and higher oral absorbability than the capsule preparations of Comparative Examples 4 and 5 which were prepared without wet granulation.

TEST EXAMPLE 4

Using 0.2 g (corresponding to 0.01 g of the medicament) of the solid compositions obtained in Examples 12 and 13 and Comparative Examples 6 and 7, the solubility of Compounds (Ib) and (Ic) were measured in the same manner as in Test Example 1. Table 4 shows the results.

TABLE 4

| Changes in solubility of compound (Ib) and compound (Ic) Dissolution test in 20 ml of water at 37° C. | | | | |
|---|---|---|---|---|
| | Solubility (μg/ml) | | | |
| | 5 min | 15 min | 30 min | 60 min |
| Example 12 | 67.5 | 54.4 | 48.7 | 52.1 |
| Example 13 | 47.9 | 55.0 | 39.0 | 29.7 |
| Comparative Example 6 | 5.9 | 7.9 | 4.0 | 2.0 |
| Comparative Example 7 | 1.7 | 1.8 | 1.9 | 1.9 |

As is apparent from Table 4, the solid compositions according to the present invention (Examples 12 and 13) showed higher solubility than the solid compositions of Comparative Examples 6 and 7 which were prepared without wet granulation.

TEST EXAMPLE 5

A solid composition obtained in the same manner as in Example 4 was stored at 40° C. under a relative humidity (RH) of 75% for 3 months. Using the solid composition before and after the storage, the solubility of Compound (Ia) was examined in the same manner as in Test Example 1. Table 5 shows the results.

TABLE 5

| Dissolution test in 20 ml of water at 37° C. | | | | |
|---|---|---|---|---|
| | Solubility (μg/ml) | | | |
| | 5 min | 15 min | 30 min | 60 min |
| Before storage | 27.0 | 27.4 | 20.4 | 29.5 |
| After storage | 22.8 | 23.3 | 23.4 | 24.0 |

As is apparent from Table 5, even after storage at 40° C. under a relative humidity (RH) of 75% for 3 months, the solid composition of the present invention (Example 4) showed high solubility in the same manner as in the level before the storage. Namely, it showed excellent temperature- and humidity-stability.

TEST EXAMPLE 6

An amount corresponding to 10 mg of Compound (IIa) or (IIIa) of each of the powdery solid compositions obtained in Examples 14 and 15 and Comparative Examples 8 and 9 was dropped into 20 ml of water at 37° C. Under paddle-stirring at 50 rpm, the solution was sampled at 0.5 ml with the lapse of time and filtered through a filter having a pore size of 0.8 μm. Then, the solubility of Compound (IIa) or (IIIa) was measured by a high-performance liquid chromatography.

Table 6 shows changes in solubility of each medicament with the lapse of time.

TABLE 6

| Dissolution test in 20 ml of water at 37° C. | | | | |
|---|---|---|---|---|
| | Solubility (μg/ml) | | | |
| | 5 min | 15 min | 30 min | 60 min |
| Example 14 | 7.2 | 7.2 | 6.6 | 6.6 |
| Example 15 | 20.1 | 19.2 | 19.7 | 19.1 |
| Comparative Example 8 | 2.4 | 1.9 | 2.1 | 2.2 |
| Comparative Example 9 | 4.2 | 3.3 | 3.7 | 4.2 |

As is apparent from Table 6, the solid compositions of Examples 14 to 15 showed higher solubility of Compounds (IIa) and (IIIa) than those of Comparative Examples 8 and 9 which were prepared without wet granulation.

TEST EXAMPLE 7

An amount corresponding to 10 mg of ubidecarenone of each of the solid compositions obtained in Examples 16 to 18 and Comparative Example 10 was dropped into 20 ml of water at 37° C. Under paddle-stirring at 50 rpm, the solution was sampled at 0.5 ml with the lapse of time and filtered through a filter having a pore size of 0.8 μm. Then, the solubility of ubidecarenone was measured by a high-performance liquid chromatography.

Table 7 shows changes in solubility of each medicament with the lapse of time.

TABLE 7

| Dissolution test in 20 ml of water at 37° C. | | | | |
|---|---|---|---|---|
| | Solubility (μg/ml) | | | |
| | 5 min | 15 min | 30 min | 60 min |
| Example 16 | 18.5 | 18.8 | 21.1 | 19.8 |
| Example 17 | 115.6 | 107.1 | 97.3 | 120.2 |
| Example 18 | 34.9 | 29.5 | 27.2 | 29.6 |
| Comparative Example 10 | 0.2 | 0.3 | 0.3 | 0.3 |

As is apparent from Table 7, the solid compositions of Examples 16 to 18 showed higher solubility of ubidecarenone than that of Comparative Example 10 which was prepared without wet granulation.

TEST EXAMPLE 8

An amount corresponding to 10 mg of Compound (Ib) of each of the solid compositions obtained in Examples 19 to 27 was dropped into 20 ml of water at 37° C. Under paddle-stirring at 50 rpm, the solution was sampled at 0.5 ml with the lapse of time and filtered through a filter having a pore size of 0.8 µm. Then, the solubility of Compound (Ib) was measured by a high-performance liquid chromatography.

Table 8 shows changes in solubility of Compound (Ib) with the lapse of time.

TABLE 8

Dissolution test in 20 ml of water at 37° C.

| | Solubility (µg/ml) | | | |
|---|---|---|---|---|
| | 5 min | 15 min | 30 min | 60 min |
| Example 19 | 227.1 | 226.6 | 229.4 | 228.6 |
| Example 20 | 28.6 | 20.5 | 18.0 | 13.6 |
| Example 21 | 62.4 | 64.7 | 59.2 | 42.2 |
| Example 22 | 85.1 | 82.9 | 82.6 | 82.6 |
| Example 23 | 66.1 | 73.1 | 70.7 | 65.7 |
| Example 24 | 84.1 | 84.1 | 82.6 | 80.6 |
| Example 25 | 71.9 | 73.4 | 69.2 | 69.1 |
| Example 26 | 72.4 | 72.6 | 67.0 | 67.2 |
| Example 27 | 74.7 | 74.4 | 68.5 | 64.5 |

As is apparent from Table 8, the solid compositions of Examples 19 to 27 showed significantly higher solubility of Compound (Ib) than that of Comparative Example 6 which was prepared without wet granulation.

TEST EXAMPLE 9

Oral absorbability (dog) of the capsule preparations obtained in Examples 28 to 31 was evaluated. One capsule of each preparations was orally administered to a beagle and the blood of the animal was collected at definite intervals. Next, the concentration of Compound (Ib) in the plasma was measured by high-performance liquid chromatography. The pharmacodynamic parameter was calculated by determining the mean and standard deviation of 3 or 4 cases. Furthermore, 10 ml of the injection of Comparative Example 11 was intravenously administered and blood collection, measurement and calculation were carried out in the same manner.

Figure 2:
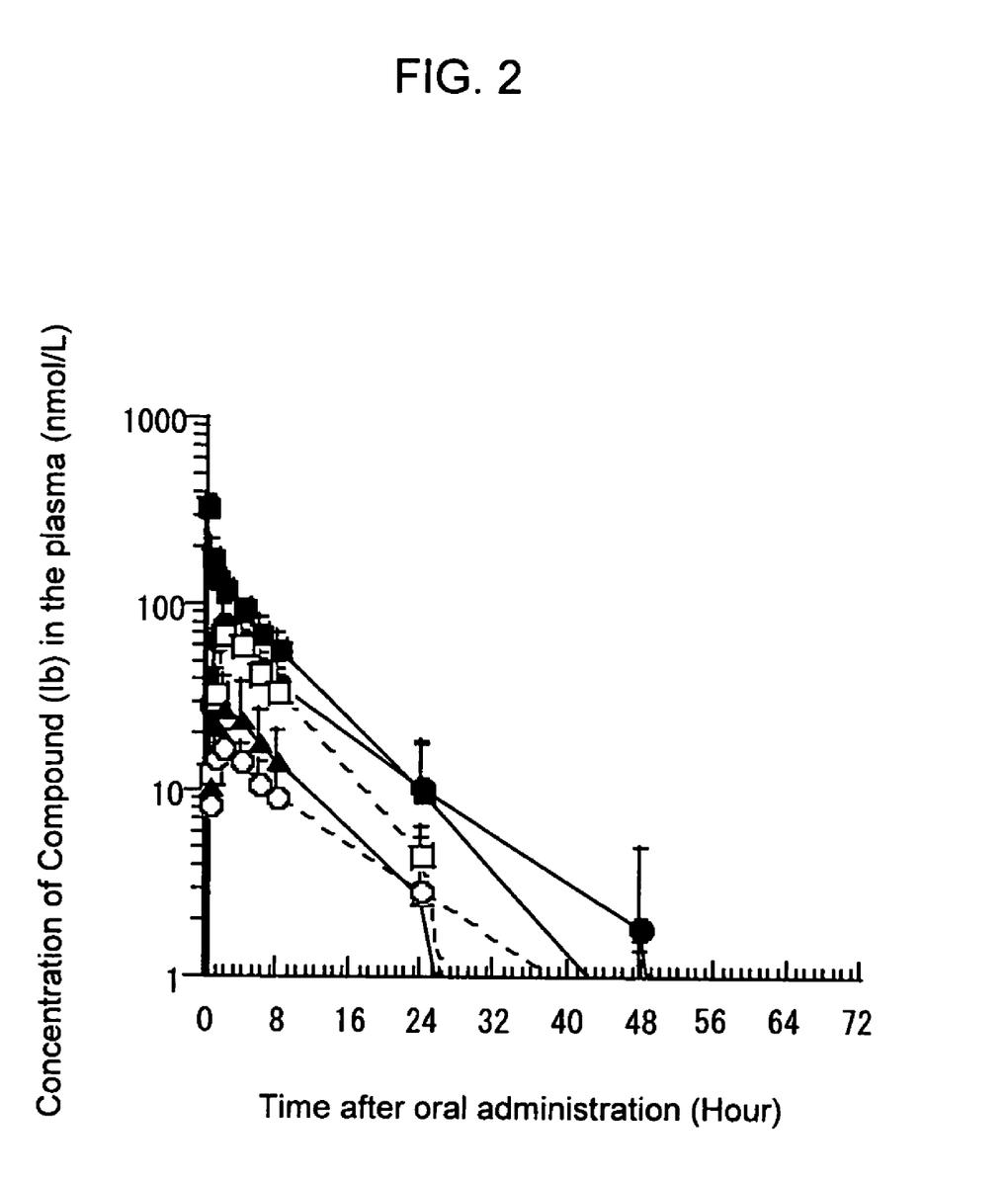
FIG. 2 shows changes in the concentration of Compound (Ib) in the plasma when a solid composition or injection each containing 0.01 g of Compound (Ib) was administered to a beagle.

FIG. 2 shows changes in the concentration in plasma and Table 9 shows pharmacodynamic parameters.

TABLE 9

| | Pharmacodynamic parameter | | | |
|---|---|---|---|---|
| | Animal number | Tmax (h) | Cmax (nmol/l) | $AUC_{0-\infty}$ (nmol · h/l) |
| Example 28 | 4 | 1.5 ± 0.6 | 84.0 ± 17.5 | 987 ± 351 |
| Example 29 | 4 | 2.0 ± 1.4 | 18.0 ± 4.1 | 247 ± 129 |
| Example 30 | 3 | 1.5 ± 0.6 | 28.6 ± 12.8 | 323 ± 127 |
| Example 31 | 4 | 2.7 ± 1.2 | 71.2 ± 29.7 | 722 ± 186 |
| Comparative Example 11 | 3 | 0.083 ± 0.0 | 337.7 ± 46.0 | 1530 ± 310 |

As is apparent from Table 9 and FIG. 2, the capsule preparations prepared by encapsulating the compositions according to the present invention correlated to the solubility shown in Table 8 and showed high oral absorbability having 16 to 65% AUC of the case of the intravenous injection (Comparative Example 11).

INDUSTRIAL APPLICABILITY

According to the present invention, a composition improved in the solubility or oral absorbability of a slightly water-soluble component can be provided.

The invention claimed is:

1. A composition which comprises three components of a medicament, a surfactant and a hydrophilic polymer, and is obtained by wet granulating in the presence of water, wherein the medicament is a compound represented by formula (I):

wherein R represents $NR_1R_2$, in which $R^1$ and $R^2$ are the same or different and each represents hydrogen, substituted or unsubstituted alkyl, substituted or unsubstituted aryl or a substituted or unsubstituted aromatic heterocyclic group, or $R^1$ and $R^2$ form a substituted or unsubstituted heterocyclic group together with the adjacent nitrogen atom, or formula (II):

wherein $R^3$ and $R^4$ are the same or different and each represents substituted or unsubstituted alkyl; and $R^5$ represents substituted or unsubstituted alkyl, substituted or unsubstituted cycloalkyl, substituted or unsubstituted bicycloalkyl, or substituted or unsubstituted tricycloalkyl.

2. The composition according to claim 1, wherein the medicament is a compound represented by formula (I) and wherein $R^1$ and $R^2$ are the same or different and each represents hydrogen or substituted or unsubstituted alkyl.

3. The composition according to claim 1, wherein the medicament is a compound represented by formula (I) and wherein $R^1$ and $R^2$ are the same or different and each represents hydrogen or alkyl having 1 to 5 carbon atoms.

4. The composition according to claim 1, wherein the medicament is a compound represented by formula (I) and wherein R is $NCH_2CH_2CH_3$, $N(CH(CH_3)_2)_2$ or $NEC(CH_3)_3$.

5. The composition according to claim 1, wherein e medicament is a compound represented by formula (IIa):

6. The composition according to claim 1, wherein the surfactant is one or more surfactants selected from the group consisting of sodium lauryl sulfate, polysorbate 80, polysorbate 60, polyoxyethylene hydrogenated, castor oil, polyoxyethylene polyoxypropylene glycol and sucrose fatty acid esters.

7. The composition according to claim 1, wherein the hydrophilic polymer is one or more hydrophilic polymers selected from the group consisting of hydroxypropyl cellulose, hydroxypropyl methyl cellulose, methyl cellulose, carboxymethyl cellulose, carboxymethyl ethyl cellulose, hydroxypropyl starch, hydroxyethyl cellulose, hydroxypropyl methyl cellulose acetate succinate, hydroxypropyl methyl cellulose phthalate, carboxyvinyl polymer, polyvinylpyrrolidone, polyvinyl alcohol, methacrylic acid copolymers, macrogol, starch, gelatin, dextrin, pullulan, agar and acacia.

8. The composition according to claim 1, wherein the hydrophilic polymer is one or more hydrophilic polymers selected from the group consisting of hydroxypropyl cellulose, hydroxypropyl methyl cellulose and polyvinylpyrrolidone.

9. The composition according to claim 1, wherein the surfactant is sodium lauryl sulfate, and the hydrophilic polymer is hydroxypropyl cellulose.

10. The composition according to claim 1, wherein the surfactant is sodium lauryl sulfate, and the hydrophilic polymer is hydroxypropyl methyl cellulose.

11. The composition according to claim 1, wherein the surfactant is sodium lauryl sulfate, and the hydrophilic polymer is polyvinylpyrrolidone.

12. The composition according to claim 1, which comprises an excipient.

13. The composition according to claim 12, wherein the excipient is one or more excipients selected from the group consisting of lactose, sucrose, starch, crystalline cellulose, D-mannitol, D-sorbitol, a starch derivative, a cellulose derivative, a carbonate, a phosphate and a sulfate.

14. The composition according to claim 12, wherein the excipient is one or more excipients selected from the group consisting of starch, crystalline cellulose and D-mannitol.

15. A method for manufacturing of a composition which comprises three components of a medicament, a surfactant and a hydrophilic polymer comprising the steps of: wet granulating the medicament together with the surfactant and the hydrophilic polymer in the presence of water, wherein the medicament is a compound represented by formula (I);

wherein R represents NR$^1$R$^2$, in which R$^1$ R$^2$ are the same or different and each re resents hydrogen, substituted or unsubstituted alkyl, substituted or unsubstituted aryl or a substituted or unsubstituted aromatic heterocyclic group, or R$^1$ and R$^2$ form a substituted or unsubstituted heterocyclic group together with the adjacent nitrogen atom, or formula (II):

wherein R$^3$ and R$^4$ are the same or different and each represents substituted or unsubstituted alkyl; and R$^5$ represents substituted or unsubstituted alkyl, substituted or unsubstituted cycloalkyl, substituted or unsubstituted bicycloalkyl, or substituted or unsubstituted tricycloalkyl.

16. The method for manufacturing according to claim 15, wherein the medicament is a compound represented by formula (I) and wherein R$^1$ and R$^2$ are the same or different and each represents hydrogen or substituted or unsubstituted alkyl.

17. The method for manufacturing according to claim 15, wherein the medicament is a compound represented by formula (I) and wherein R$^1$ and R$^2$ are the same or different and each represents hydrogen or alkyl having 1 to 5 carbon atoms.

18. The method for manufacturing according to claim 15, wherein the medicament is a compound represented by formula (I) and wherein R is NHCH$_2$CH$_2$CH$_3$, N(CH (CH$_3$)$_2$)$_2$ or NHC (CH$_3$)$_3$.

19. The method for manufacturing according to claim 15, wherein the medicament is a compound represented by formula (IIa)

20. The method for manufacturing according to claim 15, wherein the surfactant is one or mare surfactants selected from the group consisting of sodium lauryl sulfate, polysorbate 80, polysorbate 60, polyoxyethylene hydrogenated castor oil, polyoxyethylene polyoxypropylene glycol and sucrose fatty acid esters.

21. The method for manufacturing according to claim 15, wherein the hydrophilic polymer is one or more hydrophilic polymers selected from the group consisting of hydroxypropyl cellulose, hydroxypropyl methyl cellulose, methyl cellulose, carboxymethyl cellulose, carboxymethyl ethyl cellulose, hydroxypropyl starch, hydroxyethyl cellulose, hydroxypropyl methyl cellulose acetate succinate, hydroxypropyl methyl cellulose phthalate, carboxyvinyl polymer, polyvinylpyrrolidone, polyvinyl alcohol, methacrylic acid copolymers, macrogol, starch, gelatin, dextrin, pullulan, agar and acacia.

22. The method for manufacturing according to claim 15, wherein the hydrophilic polymer is one or more hydrophilic polymers selected from the group consisting of hydroxypropyl cellulose, hydroxypropyl methyl cellulose and polyvinylpyrrolidone.

23. The method for manufacturing according to claim 15, wherein the surfactant is sodium lauryl sulfate, and the hydrophilicpolymer is hydroxypropyl cellulose.

24. The method for manufacturing according to claim 15, wherein the surfactant is sodium lauryl sulfate, and the hydrophilic polymer is hydroxypropyl methyl cellulose.

25. The method for manufacturing according to claim 15, wherein the surfactant is sodium lauryl sulfate, and the hydrophilic polymer is polyvinylpyrrolidone.

26. The method for manufacturing according to claim 15, wherein the composition comprises an excipient.

27. The method for manufacturing according to claim 26, wherein the excipient is one or more excipients selected from the group consisting of lactose, sucrose, starch, crystalline cellulose, D-mannitol, D-sorbitol, a starch derivative, a cellulose derivative, a carbonate, a phosphate and a sulfate.

28. The method for manufacturing according to claim 26, wherein the excipient is one or more excipients selected from the group consisting of starch, crystalline cellulose and D-mannitol.

29. The method for manufacturing according to claim 15, wherein the wet granulating is carried out by a wet granulating method by stirring.

30. The method for manufacturing according to claim 26, wherein the wet granulating is carried out by a wet granulating method by stirring.

31. The method for manufacturing according to claim 27, wherein the wet granulating is carried out by a wet granulating method by stirring.

32. The method for manufacturing according to claim 27, wherein the wet granulating is carried out by a wet granulating method by stirring.

* * * * *

UNITED STATES PATENT AND TRADEMARK OFFICE
CERTIFICATE OF CORRECTION

PATENT NO.         : 7,125,565 B2                                      Page 1 of 1
APPLICATION NO. : 10/433515
DATED              : October 24, 2006
INVENTOR(S)        : Jun Sugishita et al.

It is certified that error appears in the above-identified patent and that said Letters Patent is hereby corrected as shown below:

Column 9, line 11, "- -" should be --•--.

Column 14, line 3, "filing" should be --filling--.

Column 22, line 14, "re resents" should be --represents--.

Column 23, line 2, "mare" should be --more--.

Signed and Sealed this

Fifteenth Day of April, 2008

JON W. DUDAS
*Director of the United States Patent and Trademark Office*